United States Patent [19]

Sekine et al.

[11] Patent Number: 4,984,566
[45] Date of Patent: Jan. 15, 1991

[54] ORTHOPEDIC CASTING TAPE

[75] Inventors: Takayuki Sekine, Kawaguchi; Naomitsu Takekawa, Tokyo, both of Japan

[73] Assignee: Tokyo Eizai Laboratory Co., Ltd., Japan

[21] Appl. No.: 403,600

[22] Filed: Sep. 6, 1989

[30] Foreign Application Priority Data

Sep. 7, 1988 [JP] Japan .................... 63-224990

[51] Int. Cl.$^5$ ............................... A61F 5/04
[52] U.S. Cl. .......................... 128/90; 428/76
[58] Field of Search ............... 128/89 R, 90, 155, 156; 428/193, 254

[56] References Cited

U.S. PATENT DOCUMENTS

| | | | |
|---|---|---|---|
| 4,376,438 | 3/1983 | Straube et al. | 128/90 |
| 4,427,002 | 2/1984 | Baron et al. | 128/83 |
| 4,502,479 | 3/1985 | Garwood et al. | 128/90 |
| 4,572,171 | 2/1986 | Wegner et al. | 128/90 |
| 4,609,578 | 9/1986 | Reed | 428/76 |
| 4,652,493 | 3/1987 | Reichmann et al. | 428/423.1 |
| 4,668,563 | 5/1987 | Buese et al. | 428/230 |
| 4,683,877 | 8/1987 | Ersfeld et al. | 128/90 |
| 4,745,912 | 5/1988 | McMurray | 128/90 |
| 4,841,958 | 6/1989 | Ersfeld et al. | 128/90 |

FOREIGN PATENT DOCUMENTS 59-6060  1/1984  Japan .

Primary Examiner—Robert A. Hafer
Assistant Examiner—Kerry Owens
Attorney, Agent, or Firm—Haverstock, Garrett & Roberts

[57] ABSTRACT

An orthopedic casting tape providing stretchability which comprises a knitted fibrous substrate impregnated with a water-curable synthetic resin wherein the substrate consists of synthetic organic fiber stretch yarn solely, in part stretch yarn and in part natural fibers, in part stretch yarn and in part artificial fibers or in part stretch yarn and in part mixtures of natural and artificial fibers. The stretch yarns are preferably those in which the stretchability is conferred by providing spiral or zigzag patterns of the synthetic fibers and utilizing the thermal plasticity and shrinkage properties of the synthetic fibers which are non-elastomeric.

13 Claims, 5 Drawing Sheets

ORTHOPEDIC CASTING TAPE

FIELD OF THE INVENTION

The present invention relates to an orthopedic casting tape which is utilized in treatment of fractures, dislocations, sprains, deformations, and other conditions in the surgical and orthopedic fields by immobilizing body members.

BACKGROUND OF THE INVENTION

Conventionally, plaster bandages made by impregnating coarse gauze with plaster of Paris have been used to immobilize body members, but this has many disadvantages, including that the plaster bandages contaminate the surrounding area by dropping plaster of Paris during treatments, and is heavy for patients and poor in permeability. Also the moisture used during curing does not evaporate for two to three days, keeping the affected portion wet for many hours, and after curing, the strength deteriorates when it makes contact with moisture. In addition, the plaster bandages absorb and disperse X-rays, preventing accurate X-ray diagnosis of the affected portion.

To replace the plaster bandage, there has been proposed a casting tape comprising a fibrous substrate which is knitted with glass fiber in tapes and coated with polyurethane resin which is wrapped around the affected portion and cured through reaction of polyurethane resin with moisture. The orthopedic casting tape using this water-curing resin has various advantages over the plaster bandage using plaster of Paris, including that it is light-weight, has good permeability, its strength does not deteriorate once it cures, and it permits better X-ray penetration.

For the fibrous substrate used in the orthopedic casting tape using a water-curing resin, nonwoven fabric, woven fabric, and knitted fabric comprising glass fiber, cotton, polyester, acrylic, polyethylene, nylon, and other materials in different forms, weight per unit area, and knitting methods have been disclosed such as in USP 4,502,479 USP 4,376,438, USP 4,652,493, USP 4,572,171, USP 4,427,002, and Japanese Unexamined Patent Application Publication No. 59-6060 (1984), among which glass fiber is particularly popular. The glass fiber is advantageous in holding strength, but has a disadvantage of poor conformability (modeling) because of its rigidity and nonstretchability. Therefore, U.S. Pat. No. 4,609,578 by Reed discloses that introduction of the knitted fabric used decreases this disadvantage by pleating or folding back the bandage when it is wrapped around the body profiles, such as around heels and elbows. U.S. Pat. No. 4,683,877 by Ersfeld et al proposes an orthopedic plaster bandage, but it is still insufficient to completely conform the fiber glass plaster bandages to the complicated curves and protrusions of a body member.

As a proposal to positively solve this problem a casting tape incorporating high modulus fibers and an elastomeric fiber has been recently announced, i.e. U.S. Pat. No. 4,668,563 of Buese and Yoon. For the high modulus fiber, glass fiber is used, and for an elastomeric fiber, natural rubber is used. Maintaining the strength with glass fiber and providing greater lengthwise extensibility with natural rubber improves the problems when the fibrous substrate comprises solely glass fiber. Any desired elasticity can be obtained by selecting the thickness and density of rubber yarns because an elastomeric fiber is used. However, with the elastomeric fiber the recovery force (force of the fiber to return to the original position when elastic goods are stretched) increases proportional to the stretching force imposed, and moreover, at the protusions or body sections where the number of bandage wraps is increased to protect and immobilize the affected portion, the recovery force is increased double to triple. Therefore, when such casting tape is applied to protrusions (in particular, edema) or lower legs with many protrusions and curves, the casting tape must be applied while stretched in order to achieve good comformability, and many wraps must be installed around articulations of feet and knees to secure proper strength, preventing the casting tape from wrapping with uniform adherence. In addition, the casting tape requires 10 minutes for apparent curing and about 30 minutes for complete curing, gradually constricting the affected portion by the recovery force during this curing time, and there is a danger of causing circulation trouble, eventually resulting in decubitus ulcers or necrosis. In addition, when glass fiber is used for the high modulus fiber, conformability to the affected portion is still not satisfactory, as discussed above. In addition, the casting tape using rubber as the elastomeric fiber tends to cure urethahe prepolymer resin earlier than intended, thus shortening the shelf life of casting tape. When using rubber as the elastomeric fiber, treatments such as solvent treatment, drying, acid treatment, and rinsing and drying are required, resulting in complexity in the manufacturing process. When using polyurethane synthetic fiber, urethane prepolmer swells the elastic yarn of polyurethane synthetic fiber, tending to degrade elasticity and requiring special processing of the fiber. Also an additional problem occurs in that the elastomeric fiber makes it difficult to cut the once-cured casting tape with a plaster bandage cutter.

The objects of the present invention are to obtain an orthopedic casting tape that is free from defects as described above of conventional casting tapes, that is, poor comformability to the affected portion, short shelf life, complicated manufacturing process, and difficultly in cutting.

SUMMARY OF THE INVENTION

According to the present invention, the aforementioned objects can be realized by an orthopedic casting tape with elasticity comprising a fibrous substrate impregnated with synthetic resin, which consists totally of stretch yarn, or in part of stretch yarn with the remainder an artificial fiber, or in part of stretch Yarn and the remainder natural and artificial fibers.

DETAILED DESCRIPTION OF THE INVENTION

Figure 1:
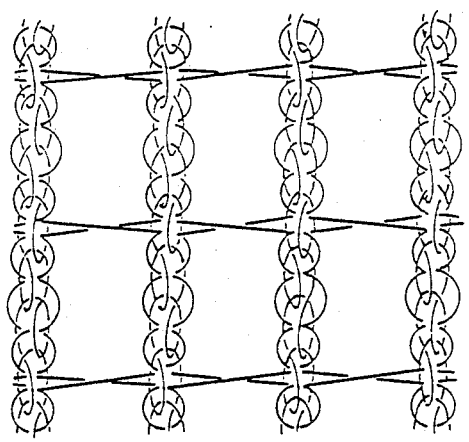
FIGS. 1 to 4 are examples of fibrous substrates of different knitting configurations according to the present invention.

The stretch yarn used in the present invention means a yarn to which elasticity is conferred by providing spiral or zigzag patterns to the fiber through utilizing thermal plasticity and shrinkage properties of the synthetic fiber, i.e. thus providing elasticity to non-elastic synthetic fiber. As for the types of stretch yarns, there are (1) stretch yarns produced by the twisting and untwisting methods, in which right-twisted and left-twisted stretch yarns are heated to fix them in the original strand condition and twist-set, then untwisted, and heat-treated, and in which one each of right-stranded and left-stranded yarns subjected to this treatment are paralleled together and lightly twisted, (2) the stretch yarns produced by the temporary twisting method, in which a yarn pulled out from a bobbin and longitudinally stretched is held at two points, twisted at midpoint to reverse the strand direction at the top and the bottom from the stranded position, the bottom half is heated and the twist fixed, then the yarn is moved from top to bottom to repeat the same procedure again, (3) the stretch yarns produced by the stuffer method, in which the yarn is folded and pressed in a cylinder and heat-treated with the yarn creased in zigzag configuration, (4) the stretch yarn produced by the edge drawing method, in which the yarn is drawn over a sharp metal knife edge, (5) the stretch yarn produced by the knit-deknit method, in which the yarn is circular-knitted in a narrow width, heat-set in a knitted form, then unknitted, (6) the stretch yarn produced by the air-jet method, in which filament yarns are disordered by injecting compressed air to form loops, and the loops are heat-set, (7) the stretch yarn produced by conjugate spinning technique, in which two solutions of components of different shrinkage percentages are spun from a spinnerette hole partitioned into two joined streams and elasticity is given by treating the two conjugated yarn parts adhered together. Polyester and polyamide yarns are two typical raw materials, but also polacrylonitrile, polyethylene, polypropylene, polyvinyl chloride, polyvinyl alcohol, and polyacetal yarns may be used.

Natural fibers which can incorporated into the stretch yarns include cotton, linen, silk, and wool.

For artificial fibers which can be used in combination with the stretch yarn, these are fibers of the same materials as the aforemetioned stretch yarn, and glass fiber, metallic fiber, carbon fiber, and boron fiber.

For the stretch yarn, it is advantageous to use a yarn formed by paralleling several strands of singles yarn comprising short or long fibers of organic synthetic fiber, such as polyester, polyamide, or polyacrylonitrile fibers. The stretch yarns are prepared by imposing sufficient tension and strongly twisting in the direction opposite to the twist of each singles Yarn, then heat-treating sufficiently as they are reverse twisted to fix the complicated deformability produced by the strong twist, then retwisting again in the opposite direction to that of the previous step to a similar level, or alternatively, by paralleling and twisting several strands of polyester conjugated yarn prior to heat-treating.

The fibrous substrate should be warp-knitted with stretch yarns arranged in the wale and/or wale and course directions.

The stretch yarn in the fibrous substrate should comprise 30–100% by volume of the fiber in the substrate.

The stretchability of the fibrous substrate in the lengthwise direction should be 20–100% under a load of 250 g/inch and that in the widthwise direction 10–250% under a like load.

As the synthetic resin to be impregnated or coated on the fibrous substrate, those which cure when reacted with water are applicable. For this type of water-curing resin, there is available polyisocyanate prepolymer. It is desirable to use polyisocyanate prepolymer comprising polypropylene oxopolyol having diphenylmethane diisocyanate as a terminal group. It is also desirable to use a synthetic resin composition comprising polyisocyanate prepolymer, benzoyl chloride as preservative, silicone as antifoaming agent, and dimethylethanolamine, bis(dimethylaminoethyl) ether, or dimorpholinodialkylether and/or mixtures thereof for catalyst to control curing time.

OPERATION OF THE INVENTION

According to the present invention, by using stretch yarn for a fibrous substrate to be impregnated or coated with resin, the casting tape provides excellent stretchability in both lengthwise and widthwise directions and conformability to optional profiles of the affected portion, and due to low modulus it does not apply excessive pressure to the affected portion. The stretch yarn is bulky, and the fibrous substrate knitted with the stretch yarns is made to be comparatively bulky, and thus is able to be impregnated or coated with a large amount of resin to produce a thickness that provides good strength and is able to be combined with the fibers other than high-modulus fiber, thereby preventing reactions of the stretch yarns with the synthetic resin, and reaction with the resin does not proceed during storage.

The following examples and discussion illustrate several desirable embodiments of the present invention.

EMBODIMENT 1

A fibrous substrate knitted on a Raschel knitting machine using the configuration as shown in FIG. 1 was used. For the chain stitch in the longitudinal direction, polyester 150 denier two-ply stretch yarns were used, and for the weft a stretch yarn of 150 denier polyester single woolly Tetron yarn was used to form a fibrous substrate with a density of 10 wales/inch and 7 courses/inch. The weight is 203 g/m$^2$, elongation percentage 64% in the weft direction and 204% in the woof direction under a load of 250 g/in.

EMBODIMENT 2

Figure 2:
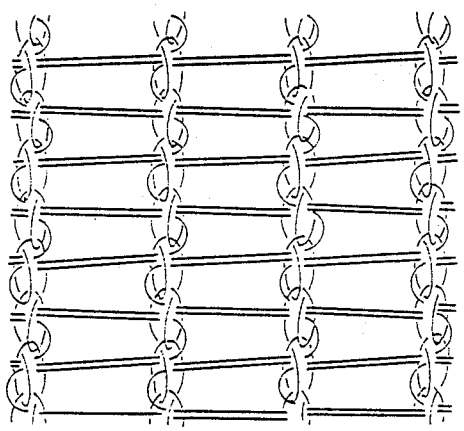

A fibrous substrate knitted on a Raschel knitting machine using the configuration as shown in FIG. 2 was used. For the chain stitch in the longitudinal direction, polyester 150 denier two-ply stretch yarns were used, and for the weft 150 denier polyester single yarns were used to form a fibrous substrate with a density of 9 wales/inch and 9 courses/inch. The weight is 205 g/m$^2$, elongation percentage 71% in the weft direction and 84% in the woof direction under a load of 250 g/inch.

EMBODIMENT 3

Figure 3:
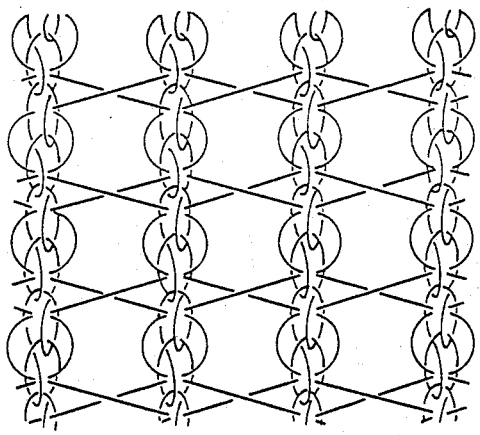

A fibrous substrate knitted on a Raschel knitting machine using the configuration as shown in FIG. 3 was used. For the chain stitch in the longitudinal direction, polyester 150 denier two-ply stretch yarns were used, and for the weft 150 denier polyester single yarns paralleled in pairs were used to form a fibrous substrate with a density of 7 wales/inch and 8 courses/inch. The weight is 169 g/m², elongation percentage 53% in the weft direction and 85% in the woof direction under a load of 250 g/inch.

EMBODIMENT 4

Figure 4:
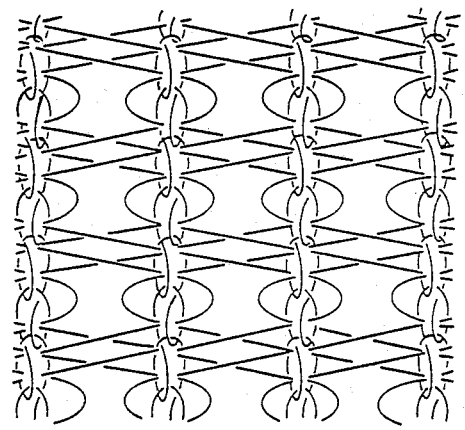

A fibrous substrate knitted on a Raschel knitting machine using the configuration as shown in FIG. 4 was used. For the chain stitch in the longitudinal direction, polyester 150 denier two-ply stretch yarns were used, and for the weft 150 denier polyester single yarns paralleled in pairs were used to form a fibrous substrate with a density of 9 wales/inch and 9 courses/inch. The weight is 186 g/m², elongation percentage 55% in the weft direction and 29% in the woof direction under a load of 250 g/inch.

EMBODIMENT 5

A fibrous substrate knitted on a Raschel knitting machine using the configuration as shown in FIG. 2 was used. For the chain stitch in the longitudinal direction, polyester 150 denier two-ply stretch yarns were used and for the weft 177 denier cotton yarns were used to form a fibrous substrate with a density of 8 wales/inch and 10 courses/inch. The weight is 160 g/m², elongation percentage 52% in the weft direction and 60% in the woof direction under a load of 250 g/in.

EMBODIMENT 6

A fibrous substrate knitted on a Raschel knitting machine using the configuration as shown in FIG. 3 was used. For the chain stitch in the longitudinal direction, nylon 180 denier two-ply stretch yarns were used, and for the weft 600 denier glass fiber yarns were used to form a fibrous substrate with the density of 12 wales-/inch and 14 courses/inch. The weight is 290 g/m2, elongation percentage 39% in the weft direction and 55% in the woof direction under a load of 250 g/inch.

EMBODIMENT 7

A fibrous substrate knitted on a Raschel knitting machine using the configuration as shown in FIG. 4 was used. For the chain stitch in the longitudinal direction, acrylic 250 denier single stretch yarns were used, and for the weft cotton-polyester mixed spinning yarns were used to form a fibrous substrate with a density of 10 wales/inch and 10 coures/inch. The weight is 170 g/m², elongation percentage 48% in the weft direction and 24% in the woof direction under a load of 250 g/inch.

EMBODIMENT 7

A fibrous substrate knitted on a Raschel knitting machine using the configuration as shown in FIG. 1 was used. For the chain stitch in the longitudinal direction, polyester 150 denier two-ply stretch yarns were used, and for the weft 177 denier cotton yarns and 180 denier polyester yarns were inserted alternately for each course in opposite directions to form a fibrous substrate with a density of 10 wales/inch and 12 courses/inch. The weight is 180 g/m², elongation percentage 56% in the weft direction and 95% in the woof direction under a load of 250 g/inch.

The properties of the eight fibrous substrates in the aforementioned embodiments are compiled in the following table

| | Embodiment | | | | | | | |
|---|---|---|---|---|---|---|---|---|
| | 1 | 2 | 3 | 4 | 5 | 6 | 7 | 8 |
| Density | | | | | | | | |
| Wales/in | 10 | 9 | 7 | 9 | 8 | 12 | 10 | 10 |
| Courses/in | 7 | 9 | 8 | 9 | 10 | 14 | 10 | 12 |
| Weight/ (g/m²) | 203 | 205 | 169 | 186 | 160 | 290 | 170 | 180 |
| Elongation percentage (%) | | | | | | | | |
| Weft | 64 | 71 | 53 | 55 | 52 | 39 | 48 | 56 |
| Woof | 204 | 84 | 85 | 29 | 60 | 55 | 24 | 95 |

Evaluation of these embodiments can be compiled in the following table, where the following marks denote;

| Embodiment | 1 | 2 | 3 | 4 | 5 | 6 | 7 | 8 |
|---|---|---|---|---|---|---|---|---|
| Easiness to wrap | | | | | | Δ | | |
| Conformability | | | | | | Δ | | |
| Smoothness of cast surface | | | | | | Δ | | Δ |
| Permeability | | | | | | | | |

Figure 5:
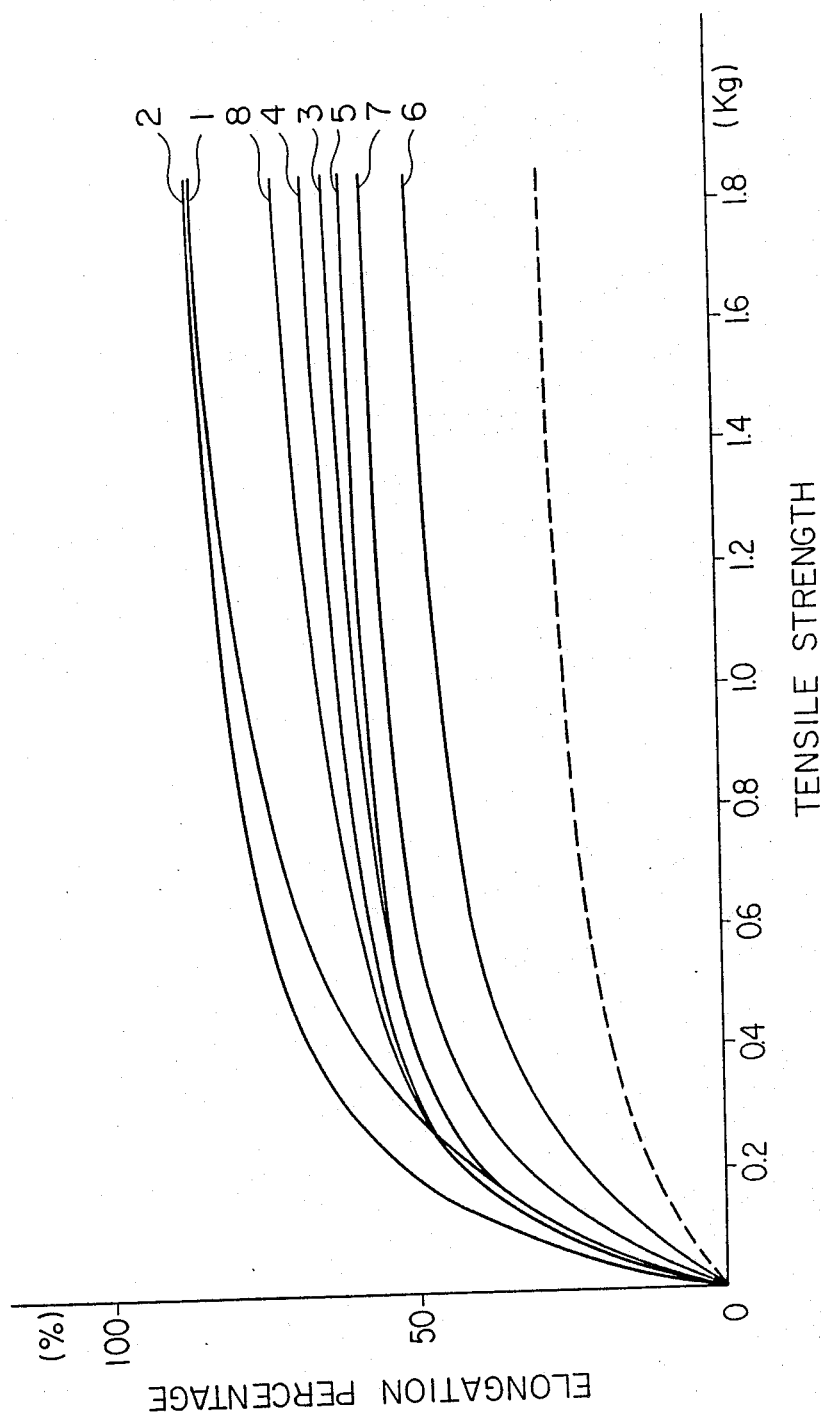
FIG. 5 is a graph of a series of elongation characteristic curves in the weft direction of the fibrous substrates according to the present invention.

Δ: Same as the conventional
 : Better than the conventional
 : Far better than the conventional FIG. 5 shows the elongation percentage of the fibrous substrates in the weft direction in each embodiment. The data were plotted with elongation percentage (%) as ordinate and tensile strength (kg) as abscissa. As specimens, a fibrous substrate of 50 mm in width and 200 mm in length was used and was stretched at the pulling rate of 100 mm/min. The number assigned to each characteristic curve shown in a solid line is the number of the aforementioned embodiment, and the characteristic curve of a glass fiber substrate is shown in a broken line for comparison. As clear from the drawing, the elongation percentage in the weft direction in all the embodiments is superior to that of a conventional glass fiber substrate.

Figure 6:
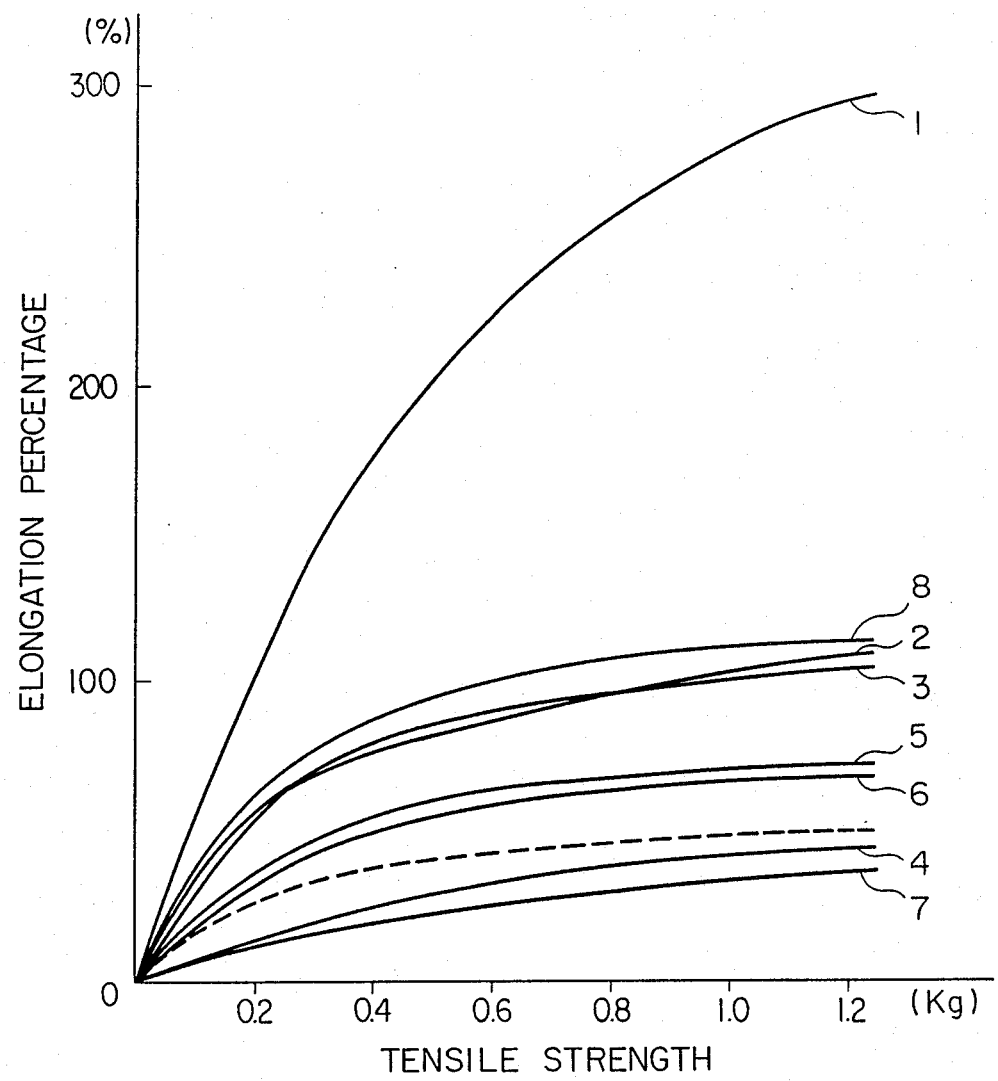
FIG. 6 is a graph of a series of elongation characteristic curves in the woof direction of the fibrous substrates according to the present invention.

FIG. 6 shows the elongation percentage of the fibrous substrates in the woof direction, with elongation percentage (%) as ordinate and tensile strength (kg) as abscissa. As specimens, a fibrous substrate 50 mm wide and 500 mm long was used and was stretched at a pulling rate of 50 mm/min. The number assigned to each characteristic curve shown in a solid line is the number of the aforemetioned embodiment, and the characteristic curve of a glass fiber substrate is shown in a broken line for comparison. As clear from the drawing, except for Embodiments 4 and 7 the elongation percentage in the woof direction is greater than that of the conventional glass fiber substrate. For Embodiments 4 and 7, the elongation percentage is smaller than that of a conventional glass fiber substrate, but what is important for the orthopedic casting tape is elongation percentage in the weft direction, and the elongation percentage in the weft direction of Embodiments 4 and 7 is superior to that of the glass fiber substrate as shown in FIG. 5, and from the general viewpoint, it is superior to that of the glass fiber substrate.

Figure 7:
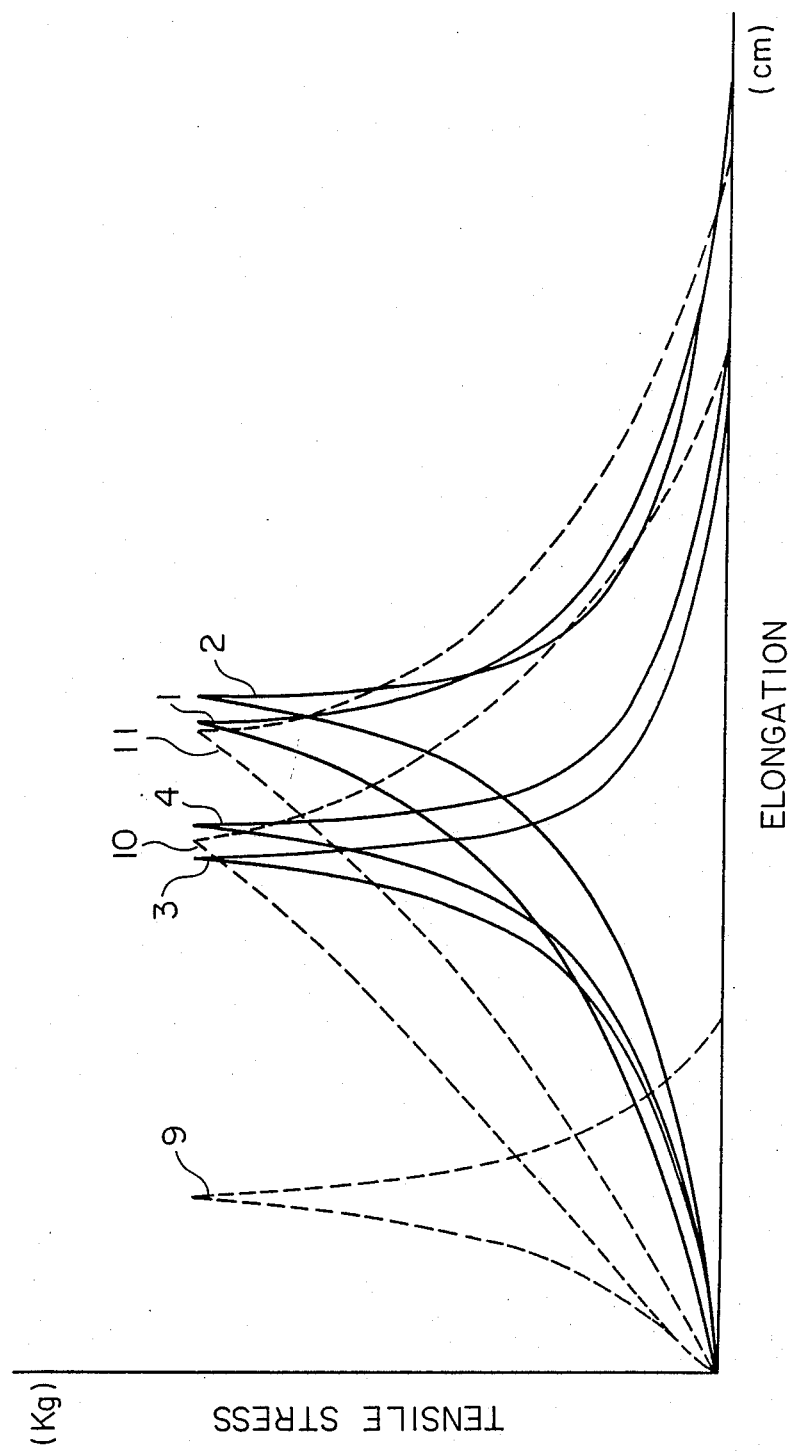
FIG. 7 is a graph comparing the stretch characteristics of the present substrates with the conventional substrates.

FIG. 7 is a characteristic curve showing the superiority of the casting tape of the present invention, especially as to stretchability, and superiority of its low recovery stress, with tensile stress taken as ordinate and elongation as abscissa. For a specimen, a fibrous substrate 50 mm wide and 200 mm long was used and elongation and stress were measured when it was stretched to a specified elongation at 100 mm/min, then returned to the original position at the same rate. The curves 1–4 show the characteristic curves for Embodiments 1–4, while curve 9 shows a characteristic curve for a glass fiber substrate. The curves 10 and 11 show characteristic curves when spandex elastomeric fiber is used for the fibrous substrate, and both fibrous substrates were knitted as follows.

Fibrous Substrate to Curve 10

A fibrous substrate knitted on a Raschel knitting machine using 500 denier polyester yarns with 140 denier spandex yarn for the chain stitch in the longitudinal direction and using polyester 500 denier yarns for the weft and a density of 13 wales/inch and 30 courses/inch was formed. The weight was 252 g/m², elongation percentage 35% in the weft direction and 66% in the woof direction under a load of 250 g/inch.

Fibrous Substrate of Curve 11

A fibrous substrate knitted on a Raschel knitting machine using 500 denier polyester yarns with 140 denier spandex yarn for the chain stitch in the longitudinal direction and using polyester 500 denier yarns for the weft with a density of 13 wales/inch and 28 courses/inch was formed. The weight was 248 g/m², elongation percentage 46% in the weft direction and 68% in the woof direction under a load of 250 g/inch.

Comparing the curves 1–4 with curves 9–11 evidences that the fibrous substrates in the embodiments of the present invention all exhibit greater elongations at a small load, indicating that they provide good conformability even without applying a large force to pull and wrap when used for an orthopedic casting tape. When curves 1–4 are compared with the curves 10 and 11 which peaks are located in the same neighborhood, curves 10 and 11 show an approximate linear stretchability against a load, whereas curves 1–4 display the feature that they require smaller tensile stress at the same elongations for they show a large curvilinear change with large elongations at a small load. Curves 1–4 have larger recoveries which is released when the stretching force is reduced from a specified load state than do curves 9–11, that is, curves 1–4 reduce recovery force dramatically by contracting only a little from the stretched condition, whereas curves 9–11 cannot reduce recovery force unless they contract considerably. When those properties are observed from the viewpoint of orthopedic casting tapes, they demonstrate that large tensile stress is not applied continuously, indicating that less constriction is produced. With the foregoing description, the fibrous substrates of the present invention provide superiority in both load at a specified elongation and elongation at a specified load over the fibrous substrates using glass fiber or spandex fiber.

According to the present invention, using stretch yarns alone or a combination of stretch yarn and natural and/or artificial fiber yarns for casting tapes in place of the conventional combination of elastomeric fiber and high-modulus fiber, realizes the following effects.

(1) The stretch yarn has a smaller modulus than the elastomeric fiber, and in particular, has a smaller force to return to the original state when the yarn is stretched (low recovery force), and therefore, there is no need to handle the casting tape with special care as to its elongation percentage in casting, requiring no special casting technique and allowing anyone to use the casting tape safely. This property renders it much easier to apply the casting tape to body members with many irregular profiles, such as wrists, elbows, knees, and articulations of the foot, or when affected portions have inflammation, because the casting tape can be applied with uniform pressure without producing any pressure difference between protruded and indented portions. Unlike the elastomeric fibers such as rubber or spandex, this low-modulus property does not increase recovery force in proportion to the number of wraps in applying the casting tape, and therefore, has the advantage of ability to apply the casting tape without producing differences of pressure due to the number of wraps accorded to the winding places, when the strength must be increased by winding many wraps, in particular to inferior limb portions. These effects are especially important in casting. If recovery force of the fibrous substrate is excessive, the fibrous substrate initiates contraction from the start of casting and during curing, constricting the affected portion to cause circulation troubles or neuroparalysis, possibly resulting in decubitus ulcers or necrosis.

(2) As to the strength property, an elastomeric fiber is high-density fiber, whereas the stretch yarn itself is a comparatively bulky yarn laid in a spiral or zigzag pattern. Therefore, the fibrous substrate knitted from the stretchable yarns is also bulky, allowing it to be impregnated by a large amount of resin; the fibrous substrate thickness is thus increased and the cured cast increases in strength. Consequently, even if especially high-modulus fiber is not used, using the fibrous substrate comprising the stretchable yarn alone or in combination with natural and/or artificial fibers and excluding high modulus fibers together with the impregnating resin can realize an orthopedic casting tape with strength enough to hold the affected portion. Because the content of high-modulus fiber can be brought to zero or to a minimum, the finished cast has a slight resilience, with comparatively higher resilience at both ends of the cast in particular, thus preventing irritation to the skin, and can be easily cut with a regular casting cutter to remove the cast. The easy cutting reduces heat generation during cutting, also reducing the possibility of burns. Less entrainment of glass fibers in the cut pieces reduces irritation to the skin caused by the cut pieces. The orthopedic casting tape which does not contain the high-modulus fiber melts or decomposes with heat allowing a cutter with a hot blade (100–600° C.) to cut easily. Consequently, the metallic noise due to high-speed microvibrations generated by a regular plaster bandage cutter is not generated, liberating the patient from a fear when his plaster bandage is cut as if with a rotating circular saw. The operator is also free from numbness caused by vibrations, allowing him to make delicate cuts.

(3) The cast provides good X-ray penetration and the discarded cast can be safely incinerated. Because the comsumption of high-modulus fiber can be zero or minimized, the fibrous substrate is made soft and free from deformation, and the processing procedure is extremely easy. Also the cast ends become difficult to peel, producing a beautiful finish without peeling even if a resin with little self-adherence is used.

(4) Because the stretch yarn does not require any chemical treatment and has no active group that reacts with isocyanate groups contained in the polyurethane resin, it can be impregnated or coated directly with resin without requiring treating with acid, alkali, or water in the fibrous substrate treatment process, and no chemical reaction takes place during storage, allowing long-term storage.

Thus, there has been shown and described an orthopedic casting tape which meets all of the objects of the present invention. It will be apparent to those skilled in the art, however that many changes, modification, variations and applications for the subject tape are possible and all such changes, modifications, variations and applications which do not depart from the spirit and scope of the invention are deemed to be covered by the invention which is only limited by the following claims.

What is claimed is:

1. An orthopedic casting tape comprising a fibrous substrate impregnated with synthetic resin, which fibrous substrate is knitted with non-elastomeric organic synthetic fiber stretch yarns in which singles yarns are paralleled, twisted and heat treated in said twisted form and wherein the twist imparted to said paralleled singles yarns in which singles yarns are paralleled, twisted and heat treated in said twisted form and wherein the twist imparted to said paralleled singles yarns reverse to the original twist of each twisted singles yarn and said reverse twisted yarns are thereafter retwisted to a similar and opposite level.

2. The orthopedic casting tape according to claim 1 wherein the fibrous substrate is knitted in part with the said stretch yarns and in part with natural fiber yarn.

3. The orthopedic casting tape according to claim 1 wherein the fibrous substrate is knitted in part with the said stretch yarns and in part with artificial fiber yarn.

4. The orthopedic casting tape according to claim 1 wherein the fibrous substrate is knitted in part with the said stretch yarns and in part with a mixture of natural fiber and artificial fiber yarns.

5. An orthopedic casting tape comprising a fibrous substrate impregnated with synthetic resin, which substrate is knitted with stretch yarns consisting of organic synthetic fibers, in which singles yarns are paralleled in several strands and sufficient tension and strong twist reversal applied to said paralleled singles yarns opposite to the original twist of each singles yarn, then heat-treated while reverse twisted to fix the complicated deformability generated by the strong twist reversal, and thereafter retwisted to a similar and opposite level.

6. The orthopedic casting tape of claim 5 using polyester, nylon, or acrylic fibers as said organic synthetic fibers.

7. The orthopedic casting tape of claim 1 wherein the fibrous substrate comprises a warp-knitted fibrous substrate in which the soul stretch yarns are knitted in the wale direction.

8. The orthopedic casting tape of claim 1 wherein the fibrous substrate comprises a warp-knitted fibrous substrate in which the said stretch yarns are knitted in both the wale and course directions.

9. The orthopedic casting tape of claim 1 wherein the said stretch yarns comprise 30–100% by volume of the total fibers in the fibrous substrate.

10. The orthopedic casting tape of claim 1 wherein the fibrous substrate before impregnation has a stretchability in the lengthwise direction of 20–100% elongation under a load of 250 g/in and a stretchability in the widthwise direction of 10–250% elongation under a load of 250 g/in.

11. The orthopedic casting tape of claim 5 wherein the fibrous substrate before impregnation has a stretchability in the lengthwise direction of 20–100% elongation under a load of 250 g/in and in the widthwise direction of 10–250% elongation under a load of 250 g/in.

12. The orthopedic casting tape of claim 5 wherein the said stretch yarns comprise 30–100% by volume of the total fibers in the fibrous substrate.

13. The orthopedic casting tape of claim 1 wherein the organic synthetic fiber stretch yarns are polyester conjugate yarns paralleled and twisted prior to heat-treating.

* * * * *

UNITED STATES PATENT AND TRADEMARK OFFICE
CERTIFICATE OF CORRECTION

PATENT NO. : 4,984,566
DATED : January 15, 1991
INVENTOR(S) : Sekine et al

It is certified that error appears in the above-identified patent and that said Letters Patent is hereby corrected as shown below:

Column 3, line 45, after "can" insert -- be --

Column 10, line 16, after "wale" delete --and course--

Signed and Sealed this

Second Day of June, 1992

Attest:

DOUGLAS B. COMER

Attesting Officer

Acting Commissioner of Patents and Trademarks